United States Patent [19]

Floyd, Jr. et al.

[11] 4,233,231
[45] Nov. 11, 1980

[54] NOVEL VINYL-STANNYL DERIVATIVES

[75] Inventors: Middleton B. Floyd, Jr., Suffern; Charles V. Grudzinskas, Nyack, both of N.Y.; Sow-Mei L. Chen, Park Ridge, N.J.

[73] Assignee: American Cyanamid Company, Stamford, Conn.

[21] Appl. No.: 853,941

[22] Filed: Nov. 22, 1977

[51] Int. Cl.$^3$ ............................................. C07F 7/22
[52] U.S. Cl. ............................ 260/429.7; 260/345.1; 568/674; 556/482
[58] Field of Search ..................................... 260/429.7

[56] References Cited
U.S. PATENT DOCUMENTS 4,038,308  7/1977  Strike .......................... 260/429.7 X
4,087,447  5/1978  Collins et al. ..................... 260/429.7

Primary Examiner—Helen M. S. Sneed
Attorney, Agent, or Firm—Richard J. Hammond

[57] ABSTRACT

Vinylstannyl derivatives and the processes for their conversion to vinyliodides, vinylbromides and vinyllithium reagents. The vinylstannyl, vinyliodides, vinylbromide derivatives and vinyllithiums are useful as intermediates for the preparation of prostaglandin analogs.

21 Claims, No Drawings

NOVEL VINYL-STANNYL DERIVATIVES

BACKGROUND OF THE INVENTION

The prostagladins are currently of great interest because of the broad physiological responses which they elicit in animals, including man.

Development of the potential application of both natural and synthetic prostaglandins relies upon efficient chemical synthetic methods being available.

Processes for preparing prostaglandins and derivatives via a conjugate addition process have been described in U.S. Pat. Nos. 3,965,143 and 3,950,406, and Tet. Letters, No. 4, 235 (1976) and Prostaglandins, 10 733 (1975).

Each of the following references utilize a hydroxy protected vinyliodide such as A, B or C:

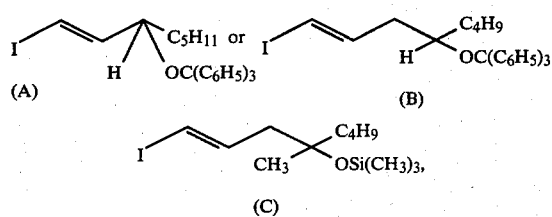

as described, among others, in U.S. Pat. Nos. 3,962,351; 3,962,352; 3,962,353; 4,007,210; 3,932,479; 3,965,143; and 3,950,406.

Recently E. J. Corey [Journ. Org. Chem. Soc., 40, 2265 (1975)] described the preparation of the vinylstannane D, and more recently [Journ. Amer. Chem. Soc., 98, 222 (1976)] the vinylstannyl derivative E.

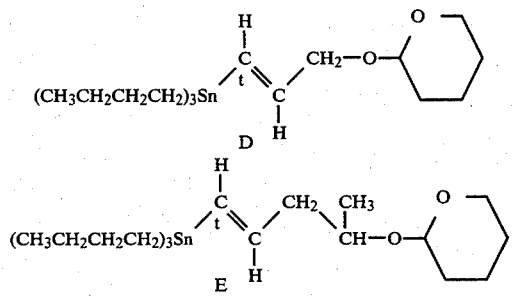

SUMMARY OF THE INVENTION

It is the purpose of this invention to provide novel vinylstannyl compounds as key intermediates in the conjugation addition process to produce prostaglandin analogs. In addition, these novel vinylstannyl derivatives can be utilized to provide the corresponding vinyliodides in high yields, thereby increasing the efficiency of the corresponding acetylene to vinyliodide conversion.

DISCLOSURE

The vinylstannyl derivatives of this invention can be prepared from the corresponding acetylene as described in Flowsheet A. In accordance with Flowsheet A, an acetylene 1 is treated with tri-n-butylstannane in the presence of azobisisobutyronitrile wherein $R_1'$ is:

wherein $R_5$ is selected from the group consisting of $C_4$–$C_7$ alkyl;

$R_6$ is selected from the group consisting of $C_5$–$C_6$ alkyl;

$R_7$ is selected from the group consisting of $C_2$–$C_5$ alkyl;

$R_8$ is methyl or ethyl;

$R_{10}$ is selected from the group consisting of $C_1$–$C_4$ alkyl;

$R_{11}$ is selected from the group consisting of $C_3$–$C_6$ alkyl, benzyl, 2-butyne, and 2-butene;

n is the integer 1 or 2;

p is the integer 1 or 2; and q is the integer 1 or 2.

FLOWSHEET A

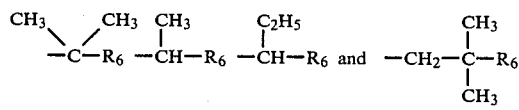

An alternate procedure to prepare precursors of 15-hydroxy prostanoic acids is described in Flowsheet B. In accordance with Flowsheet B, an appropriate aldehyde 3 or methyl ketone 6 is treated with E-1-lithium-2-(tri-n-butylstannyl)ethylene [Nesmeyanov, Dokl. Akao. Navk. S.S.R., 174, 196.(1967); E. J. Corey, Journ. Amer. Chem. Soc., 96, 5581 (1974)] or other E lithium triloweralkylstannyl ethylene derivatives to provide the corresponding E vinylstannyl alcohol 4 and 7. Treatment of the alcohols 4 or 7 with an appropriate hydroxyl protecting group such as $(CH_3)_3SiCl$ or $(C_2H_5)_3SiCl$ or other known protecting groups then provides the vinylstannyl silyl ethers 5 and 8, respectively, wherein $R_3$ is $CH_3$ or $C_2H_5$, $R_5$ and $R_6$ are as herein above defined, and $R_{12}$ is a moiety selected from the group consisting of:

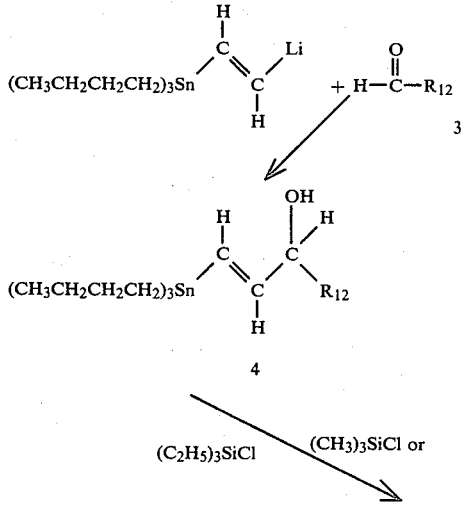

-continued
FLOWSHEET B

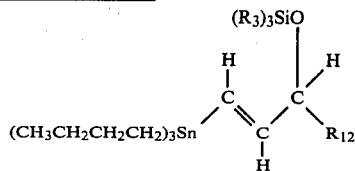

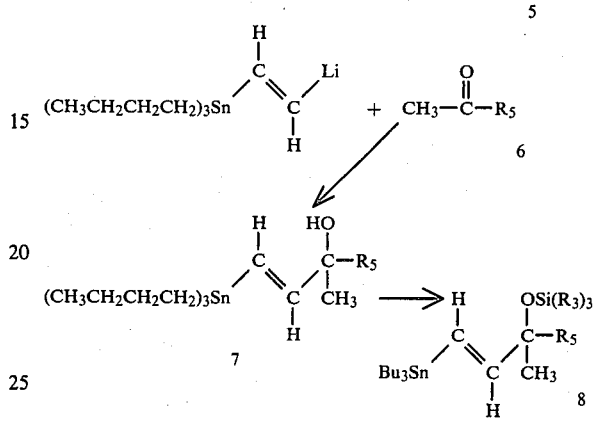

The novel vinylstannyl derivatives of this invention can be utilized in two ways.

If the hydroxyl-protected vinylstannyl derivatives 5 and 7 are treated with one equivalent of n-butyllithium in a solvent such as tetrahydrofuran at −70° to −10° C., the corresponding vinyllithium is generated. These vinyllithiums can then be utilized via symmetric or asymmetric cuprate formation to provide the corresponding prostaglandin as illustrated in Flowsheet C for a 15-hydroxy prostaglandin of the $E_2$ series. This process is applicable to other prostaglandin analogs.

FLOWSHEET C

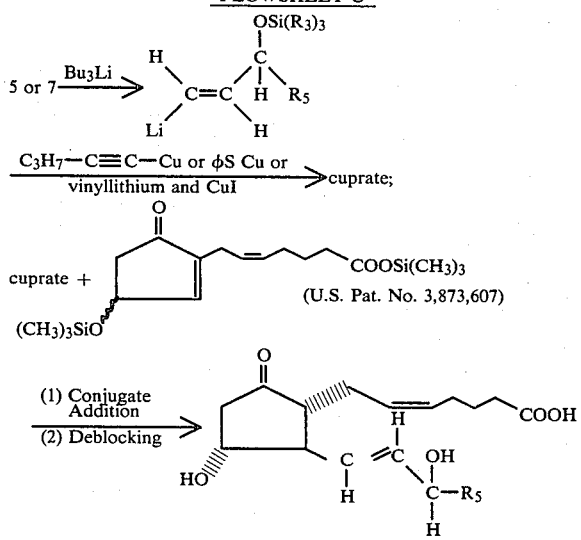

In addition, the novel vinylstannyl derivatives 2 of this invention can be converted to the corresponding vinyliodides 9 and vinylbromides 10 by treatment with one equivalent of iodine in an organic solvent such as ether as shown in Flowsheet D or with one equivalent of bromine in an organic solvent such as carbontetrachloride as shown by Rosenbert, Journ. Amer. Chem. Soc., 79, 2138 (1957).

These vinyliodides 9 and vinylbromides 10 are also precursors for the preparation of prostaglandins via a conjugate addition by method known in the art.

FLOWSHEET D

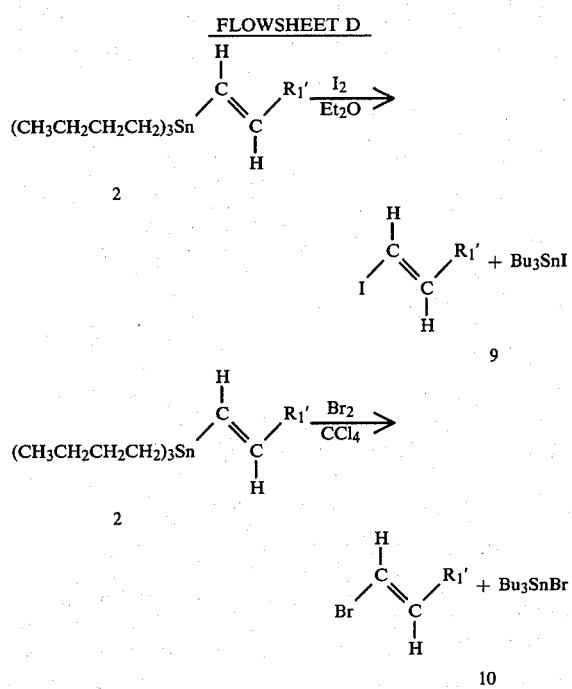

DETAILED DISCLOSURE

EXAMPLE 1

Preparation of 3-triethylsilyloxy-1-octyne

To a magnetically stirred solution of 50 g of 1-octyn-3-ol, 83 g of imidazole, and 500 ml of anhydrous dimethylformamide, cooled in an ice-water bath under an argon atmosphere, is slowly added 90 g of chlorotriethylsilane. After several minutes the reaction mixture is warmed to ambient temperature, and the progress of the reaction is monitored by tlc (1:4/ethyl acetate:benzene). On completion, the reaction mixture is poured into 500 ml of an iced mixture of 1:1 hexane-water. The organic phase is separated, washed with water and brine, dried over sodium sulfate and concentrated in vacuo. The resulting oil is distilled to provide 83 g (bp 70°–72° C., 0.35 mm).

EXAMPLE 2

Preparation of (E)-1-tri-n-butylstannyl-3-triethylsilyloxy-1-octene

A solution of 20 g of 3-triethylsilyloxy-1-octyne, 150 mg of azobisisobutyronitrile, and 30 ml of tri-n-butyltin hydride is magnetically stirred under an argon atmosphere at 140° C. for 2 hours, (EXOTHERMIC), then cooled to ambient temperature. The excess tin hydride is removed by distillation (~70°/1.0 mm). The residue is purified by distillation to provide 36.5 g of the oil (bp 165° C. at 0.05 mm).

EXAMPLE 3

Preparation of 1-octyn-4-ol

A suspension of 24.3 g (1.0 mole) of magnesium in 90 ml of dry ether is stirred at room temperature under nitrogen with 100 mg of mercuric chloride. The reaction is initiated by the addition of 2 ml of propargyl bromide and maintained by the dropwise addition of a solution of 119.5 g (1.0 mole) of propargyl bromide and 107.7 g. (1.25 mole) of valenaldehyde in 300 ml of dry ether. While the initial reaction is quite vigorous and is maintained at 30° C. only by cooling in an ice bath it may become necessary to heat the mixture to reflux temperature after about a third of the ether solution is added in order to maintain the reaction. After the addition is complete the reaction mixture is refluxed until most of the magnesium is dissolved (several hours) and the reaction mixture is decanted from excess magnesium into 1500 ml of stirred ice-cold ammonium chloride solution. The ether layer is separated and the aqueous layer is extracted three times with 300 ml portions of ether. The combined ether extract is washed with saturated sodium chloride solution, dried over magnesium sulfate and filtered. Evaporation of the ether under vacuum leaves about 115 g of yellow oil, which is distilled through a 15 cm Vigreaux column at 18 mm. The fraction boiling at 81°–82° C. is collected (36 g) and the higher-boiling and lower-boiling distillates may be redistilled to yield additional product. The infrared absorption spectrum shows at most a trace of allene (5.1μ) and gas-liquid partition chromatography shows a purity of about 98% for the main fraction.

EXAMPLES 4–17b

The product 1-alkyn-4-ols of Table I below are prepared by treatment of the aldehydes and ketones listed in Table I with propargyl magnesium bromide by the procedure described above in Example.

TABLE I

| Example | Starting Aldehyde | Product 1-alkyn-4-ol |
|---|---|---|
| 4 | n-hexaldehyde | 1-nonyn-4-ol |
| 5 | n-heptaldehyde | 1-decyn-4-ol |
| 6 | n-butyraldehyde | 1-heptyn-4-ol |
| 7 | 2-octanone | 4-methyl-4-hydroxy-1-decyne |
| 8 | trans-2-hexenal | 4-hydroxy-5-trans-nonen-1-yne |
| 9 | 2,2-dimethylhexanal | 5,5-dimethyl-4-hydroxy-1-nonyne |
| 10 | 2-heptanone | 4-methyl-4-hydroxy-1-nonyne |
| 11 | 2,2-dimethylpentanal | 5,5-dimethyl-4-hydroxy-1-octyne |
| 12 | 2-methylpentanal | 5-methyl-4-hydroxy-1-octyne |
| 13 | 2-methylhexanal | 5-methyl-4-hydroxy-1-nonyne |
| 14 | 2-hexanone | 4-hydroxy-4-methyl-1-octyne |
| 15 | trans-3-hexen-2-one[a] | 4-hydroxy-4-methyl-5-trans-octen-1-yne |
| 16 | trans-2-pentenal[b] | 4-hydroxy-5-trans-octen-1-yne |
| 17 | trans-2-heptenal[b] | 4-hydroxy-5-trans-de-en-1-yne |
| 17a | cyclohexanone | 1-(2-propynyl)-cyclohexan-1-ol |
| 17b | cyclopentanone | 1-(2-propynyl)-cyclopenten-1-ol |

EXAMPLE 18

Preparation of 4-benzoyloxy-1-octyne

To a stirred solution of 63. g (0.50 moles) of 1-octyn-4-ol (Example 93) in 500 ml of pyridine is added 77 g (0.55 moles) of benzoyl chloride. After stirring for 1.5 hours the mixture is treated with 10 ml of water, allowed to stand for 15 minutes, and concentrated. A solution of the residue in ether is washed successively with ice-cold hydrochloric acid, water, sodium bicarbonate solution, and brine. The solution is dried over magnesium sulfate, filtered through Celite, and concentrated to give an oil, λ max. 3240 (terminal acetylene) and 1730 cm$^{-1}$ (benzyloxy group).

EXAMPLE 19

Stereoselective Hydrolysis of Racemic 4-benzoyloxy-1-octyne by Rhizopus arrhizus An agar slant of R. arrhizus (MUMF 1638) is used to inoculate 7 shake flasks (250 ml Erlenmeyer). Each flask contains 50 ml of a medium consisting of 2% Edamine, 2% glucose, and 0.72% corn steep liquor in water with pH adjusted to 7.0. A total of 14 such flasks are incubated on a rotary shaker at 28° C. After 72 hours incubation, 50 mg of racemic 4-benzoyloxy-1-octyne (Example 18) in 0.1 ml of acetone is added to each flask. After 28 hours the flasks are harvested and worked up by extraction of the whole mash with an equal volume of chloroform. The combined extracts are dried over magnesium sulfate and concentrated. The resulting oil is chromatographed on a column of silica gel with hexane progressively enriched in ethyl acetate.

From fractions 3–6 is obtained 150 mg of colorless oil, identical to 4-benzoyloxy-1-octyne, $[\alpha]_D^{25} = 5° \pm 1.0°$ (C=0.91, ethyl acetate). This compound has the (S)-configuration.

From fractions 13–20 is obtained 75 mg of colorless oil, identical to 4-hydroxy-1-octyne, $[\alpha]_D^{25} = -17° \pm 1.0°$ (C=0.77, ethyl acetate). This compound has the (R)-configuration.

The strain of R. arrhizus utilized in this experiment is a higher fungus which grows steadily on a variety of artificial media at 20°–25° C. In this study of the taxonomic aspects of the culture, Petri dishes of potato-dextrose, malt extract, and cornmeal agars were inoculated and incubated at ambient room temperature for 10 days. Observations of cultural and morphological characteristics are recorded in the description below:

Colonies on Petri dishes of potato-dextrose agar growing rapidly, covering the agar surface in 3–5 days and producing a thick, loose mat of grayish mycelium. Colony surface characterized by abundant black sporangia. Colony reverse grayish white. Colonies on malt extract agar growing rapidly, covering the agar surface in 3–5 days. Mycelial mat thick, grayish-yellow. Colony surface becoming brownish-black from masses of sporangia. Colony reverse yellowish. Colonies on cornmeal agar very thin, whitish; spreading across agar surface. Cultures transparent with relatively few sporangia produced. Visibility of micromorphology is good on this medium. Rhizoids produced sparingly along stoloniferous hyphae. Generally two to three sporangiophores arose from rhizoids. Walls of sporangiophores oliv brown, 14.0–20.0 μm in width at base, tapering slightly to apex; 0.5–1.5 mm in length. Sporangiophores terminated by spherical sporangia, 130–225 μm in diameter. Columellae hemispherical, 3–50 μm high by 50–70 μm wide. Spores brownish when mature, 6.0–8.5 μm×4.5–6.0 μm. Spore walls conspicuously marked by longitudinal striations.

EXAMPLE 20

Preparation of (S)-4-hydroxy-1-octyne

A solution of 1.15 g (5.0 mmoles) of (S)-4-benzoyloxy-1-octyne (Example 19) and 1.40 g (25 mmoles) of potassium hydroxide in 50 ml of 10:1 methanol-water is allowed to stand at toom temperature for 24 hours. The bulk of the methanol is evaporated at room temperature, and the mixture is extracted with ether. The extract is washed with brine, dried over magnesium sulfate, and evaporated to give a colorless oil, identical to 4-hydroxy-1-octyne $[\alpha]_D^{25} = +17° \pm 1.0°$ (C=0.77, ethyl acetate). This compound has the (S)-configuration.

EXAMPLES 21–40

Treatment of the hydroxy-acetylenes of Table II with the indicated triloweralkylchlorosilane according to the procedure of Example 1 followed by treatment of the resulting silylether with tri-n-butylstannane by the procedure of Example 2 is productive of the silyloxyvinylstanne of the Table.

TABLE II

| Ex. | Starting Hydroxy Acetylene | Silyl-chloride | Product silyloxyvinylstannane |
|---|---|---|---|
| 21 | Ex. 3 | TES | (E)-4-triethylsilyloxy-1-tri-n-butylstannyl-1-octene |
| 22 | Ex. 5 | TES | (E)-4-triethylsilyloxy-1-tri-n-butylstannyl-1-decene |
| 23 | Ex. 6 | TES | (E)-4-triethylsilyloxy-1-tri-n-butylstannyl-1-heptene |
| 24 | Ex. 4 | TES | (E)-4-triethylsilyloxy-1-tri-n-butylstannyl-1-nonene |
| 25 | Ex. 7 | TMS | (E)-4-methyl-4-trimethylsilyloxy-tri-n-butylstannyl-1-decene |
| 26 | Ex. 8 | TES | (E)-4-triethylsilyloxy-1-tri-n-butylstannyl-1,5-trans-nonadiene |
| 27 | Ex. 9 | TMS | (E)-4-trimethylsilyloxy-5,5-dimethyl-1-tri-n-butylstannyl-1-nonene |
| 28 | Ex. 10 | TMS | (E)-4-methyl-4-trimethylsilyloxy-1-tri-n-butylstannyl-1-nonene |
| 29 | Ex. 11 | TMS | (E)-4-trimethylsilyloxy-5,5-dimethyl-1-tri-n-butylstannyl-1-octene |
| 30 | Ex. 12 | TES | (E)-4-triethylsilyloxy-5-methyl-1-tri-n-butylstannyl-1-octene |
| 31 | Ex. 13 | TES | (E)-4-triethylsilyloxy-5-methyl-1-tri-n-butylstannyl-1-nonene |
| 32 | Ex. 14 | TMS | (E)-4-trimethylsilyloxy-4-methyl-1-tri-n-butylstannyl-1-octene |
| 33 | Ex. 15 | TMS | (E)-4-trimethylsilyloxy-4-methyl-1-tri-n-butylstannyl-1,5-trans-octadiene |
| 34 | Ex. 16 | TES | (E)-4-triethylsilyloxy-1-tri-n-butylstannyl-1,5-trans-octadiene |
| 35 | Ex. 17 | TES | (E)-4-triethylsilyloxy-1-tri-n-butylstannyl-1,5-trans-decadiene |
| 36 | Ex. 19 | TES | (E)-4(R)-triethylsilyloxy-1-tri-n-butylstannyl-1-octene |
| 37 | Ex. 20 | TES | (E)-4(S)-triethylsilyloxy-1-tri-n-butylstannyl-1-octene. |
| 38 | 1-decyne-3-ol U.S. Pat. No. 3,873,601 Ex. 129 | TES | (E)-3-triethylsilyloxy-1-tri-n-butylstannyl-1-decene |
| 39 | 4-methyl-1-heptyne-3-ol U.S. Pat. No. 3,873,607 Ex. 132 | TES | (E)-3-triethylsilyloxy-4-methyl-1-tri-n-butylstannyl-1-octene |
| 40 | 4-ethyl-1-octyne-3-ol[1] U.S. Pat. No. 3,873,607 Ex. 130 | TES | (E)-3-triethylsilyloxy-4-ethyl-1-tri-n-butylstannyl-1-octene |
| 40a | Ex. 17a | TMS | 1-(E-3-tri-n-butylstannyl-2-propenyl)-1-trimethylsilyloxy-cyclohexane |
| 40b | Ex. 17b | TMS | 1-(E-3-tri-n-butylstannyl-2-propenyl)-1-trimethylsilyloxy-cyclopentane |

EXAMPLE 41

Preparation of 3-tetrahydropyranyloxy-1-propyne

To a stirred solution of 112 g (2.0 mol.) of 3-hydroxy-1-propyne and 260 g (3.0 mol.) of dihydropyran in 1.20 liters of methylene chloride cooled to 0° C. in an ice bath, is added a solution of 20 mg of para-toluenesulfonic acid in 100 ml of methylene chloride, dropwise. The reaction mixture is stirred at 0° C. for one-half hour, and at ambient temperature for one hour. It is then poured into 200 ml of a 5% solution of sodium bicarbonate, the organic phase is separated, the aqueous phase extracted with 100 ml of methylene chloride, the combined organic phases washed with 100 ml of a solution of brine, dried over sodium sulfate, and evaporated under vacuum (12 mm) at 45° C. to give 300 g of crude product, which is purified by fractional distillation, bp 71°–73° C. (14 mm) to yield 250 g (89%) of a liquid.

EXAMPLE 42

Preparation of 3-tetrahydropyranyloxy-1-trimethylsilyl-1-propyne

To a stirred −20° C. solution of 125 g (0.89 mol.) of 3-tetrahydropyranyloxy-1-propyne (Example 41) in 450 ml of ether, under a nitrogen atmosphere, is added dropwise, over one hour, a solution of 45 ml (0.89 mol.) of 2.0 N n-butyllithium in hexane. After 150 ml of dry ether is added and the mixture is stirred at −20° C. for 30 minutes, a solution of 98 g (0.89 mol.) of trimethylchlorosilane in 73 ml of ether is added dropwise. Stirring is continued for 30 minutes at −20° C. and at ambient temperature for 18 hours. The reaction mixture is again cooled to −20° C., and a solution of 90 ml of acetic acid in 300 ml of ether is added dropwise, followed by 90 ml of water. It is then diluted with 500 ml of water, and extracted 3 times with 300 ml of 5% sodium bicarbonate solution. The organic phase is separated, washed with 500 ml of a saturated brine solution, dried over sodium sulfate, and evaporated at 40° C. under vacuum (12 mm). The crude product is fractionally distilled, bp 120°–125° C. (18 mm), to yield 120 g of an oil.

EXAMPLE 43

Preparation of erythro-3-tetrahydropyranyloxy-4-hydroxy-1-trimethylsilyl-1-octyne To a stirred −78° C. solution of 62 ml (124 mmol.) of a 2.0 M solution of n-butyllithium in hexane and 50 ml of dry tetrahydrofuran, under a nitrogen atmosphere is added dropwise, a solution of 24 g (113 mmol.) of 3-tetrahydropyranyloxy-1-trimethylsilyl-1-propyne (Example 42) in 35 ml of tetrahydrofuran. This red solution is stirred one hour at −78° C., tehn a freshly prepared solution of zinc iodide (135 mmol.) in 125 ml of tetrahydrofuran [F. Mercier, R. Eqsztein, and S. Holand, Bull. Soc. Chim. Franc, 2, 690 (1972)] is added dropwise at −78° C. until the mixture turns yellow. After stirring an additional hour at −78° C., a solution of 21 g (250 mmol.) of n-valeraldehyde in 35 ml of tetrahydrofuran is added dropwise and the reaction mixture stirred for one hour at −78° C. and 18 hours at ambient temperature. It is then cooled to 0° C. and a solution of 12 ml of acetic acid in 65 ml of ether is added dropwise, followed by 75 ml of ice-water. The phases are separated and the aqueous phase is extracted twice with ether. The combined organic phases are washed 3 times with saturated sodium bicarbonate solution, until the last wash is basic, then with a saturated brine solution, dried over sodium sulfate, and evaporated to give 40 g of yellow oil. The crude product may be purified on a 4″×40″ dry column of alumina, and eluted with chloroform. I.R.: neat; 3550 (OH), 2200 (C≡C), 840, 750[(CH$_3$)$_3$Si], cm$^{-1}$.

EXAMPLE 44

Preparation of erythro-3,4-dihydroxy-1-trimethylsilyl-1-octyne

A solution of 19.6 g (0.066 mol) of d,l-erythro-3-tetrahydropyranyloxy-4-hydroxy-1-trimethylsilyl-1-octyne (Example 43) in 55.5 ml of ethanol, 22.2 ml of acetic acid, and 22.2 ml of water is heated at reflux for 3 hours. The cooled mixture is taken to dryness and evaporated twice with benzene. The residue is taken up in hexane, washed 3 times with saturated potassium bicarbonate solution, dried with magnesium sulfate, and evaporated to give 17.0 g of crude product. IR: neat, 3500-3400, broad (two OH)

EXAMPLE 45

Preparation of erythro-3,4-isopropylidenedioxy-1-trimethylsilyl-1-octyne

To a stirred solution of 17.0 g (79.5 mmol.) of crude, d,l-erythro-15,16-dihydroxy-1-trimethylsilyl-1-octyne (Example 44) is 33.6 ml of 2,2-dimethoxy propane at 0° C., is added 0.05 ml of 60% perchloric acid. After 30 minutes at ambient temperature, the mixture is shaken with 50 ml of hexane and 25 ml of saturated sodium bicarbonate solution. The hexane phase is separated, dried with magnesium sulfate, and evaporated to give 19.0 g of crude product.

EXAMPLE 46

Preparation of erythro-3,4-isopropylidenedioxy-1-octyne

A mixture of 19.0 g (75.0 mmol.) of crude d,l-erythro-3,4-isopropylidenedioxy-1-trimethylsilyl-1-octyne (Example 45) with 95 ml of methanol and 3.0 g of potassium carbonate is refluxed for one hour. The mixture is cooled and evaporated at 50° C. (13 mm), taken up in 250 ml of benzene, and washed with 100 ml of water. The water is saturated with salt, the organic phase separated, dried with magnesium sulfate, and evaporated to give 12 g of crude product. Fractional distillation yields 7.0 g of the subject compound as a colorless oil, bp 103°–106° C. (13 mm).

IR: neat; 3300 sharp (H—C C), 2100 (C≡C), 780 (erythro configuration) cm$^{-1}$ nmr: CDCl$_3$ TMS; 4.75 (dd. l, C C—C$\underline{H}$—CH, J=2 Hz, J=5 Hz, 4.10 (m, 1, C C—CH—C$\underline{H}$—CH$_2$, 2.5 (d, 1, $\underline{H}$—C C—CH), 1.9–1.2 (m, 14, alkyl), 0.90 (m, 3H, CH$_2$CH$_3$).

EXAMPLE 47

Preparation of erythro-3-tetrahydropyranyloxy-4-acetyloxy-1-trimethylsilyl-1-octyne A solution of 3.0 g (13.2 mmol.) of erythro-3-tetrahydropyranyloxy-4-hydroxy-1-trimethylsilyl-1-octyne is heated at 100° C. for 15 hours with 3 ml of acetic anhydride and 10 ml of pyridine. The mixture is evaporated to dryness, dissolved in ether, washed with sodium bicarbonate solution and water. The organic phase is dried over magnesium sulfate and evaporated to give 2.5 g of the subject compound as an oil. IR: neat; 2200 (C≡C), 1730 (C=O), 830, 760 [(CH$_3$)$_3$Si], cm$^{-1}$.

EXAMPLE 48

Preparation of d,l-erythro-3-hydroxy-4-acetyloxy-1-trimethylsilyl-1-octyne

A solution of 2.5 g (7.4 mmol.) of erythro-3-tetrahydropyranyloxy-4-acetyloxy-1-trimethylsilyl-1-octyne (Example 47) in ethanol, acetic acid, and water is heated at 100° C. for 3 hours. After workup, the crude product is chromatographed on a ⅞"×22" dry column of silica gel, and eluted with chloroform to give 1.0 g of a yellow oil. IR: neat; 3500 (OH), 1730 (C=O), cm$^{-1}$.

EXAMPLE 49

Preparation of erythro-3-paratoluenesulfonyloxy-4-acetyloxy-1-trimethylsilyl-1-octyne To a solution of 7.5 g (41.0 mmol.) of erythro-3-hydroxy-4-acetyloxy-1-trimethylsilyl-1-octyne (Example 48) in 41 ml of dry pyridine is added 11.0 g (58 mmol.) of para-toluenesulfonyl chloride and the resulting solution is stirred at 25° C. for 15 hours. The mixture is then warmed at 40° C. for one hour, and after cooling, partitioned between 500 ml of diethyl ether and 100 ml of 1.0 N hydrochloric acid. The organic phase is washed three times with 100 ml of 1.0 N hydrochloric acid, once with dilute sodium bicarbonate solution, dried over magnesium sulfate, and evaporated under reduced pressure to give an oil. The crude product is purified on a 2"×24" dry column of silica gel, and eluted with chloroform to yield a yellow oil.

IR: neat; 1730 (C=O), 1595 (aromatic) cm$^{-1}$.

EXAMPLE 50

Preparation of threo-3-hydroxy-4-acetyloxy-1-trimethyl-silyl-1-octyne

A mixture of 15.5 g (39.0 mmol.) of erythro-3-paratoluenesulfonyloxy-4-acetyloxy-1-trimethylsilyl-1-octyne (Example 49), 5.0 g of calcium carbonate, 25 ml of water and 250 ml of tetrahydrofuran is refluxed with stirring for 4 days. The mixture is cooled, 100 ml of water added and the organic phase separated. The aqueous phase is extracted with ether, the combined organic phases dried with magnesium sulfate, and evaporated. The crude product is chromatographed on a 3"×30" dry column of silica gel, and eluted with chloroform to give 7.0 g of an oil.

IR: neat; 3500, (OH), cm$^{-1}$.

EXAMPLE 51

Preparation of threo-3,4-dihydroxy-1-octyne

A solution of 7.0 g (28 mmol.) of threo-3-hydroxy-4-acetyloxy-1-trimethylsilyl-1-octyne (Example 50) in 50 ml of methanol is stirred at room temperature for 24 hours with a solution of 6.3 g (112 mmol.) of potassium hydroxide in 50 ml of water. The mixture is extracted twice with hexane, washed with 0.5 M hydrochloric acid, brine, and dried with magnesium sulfate. After evaporation, the subject compound is obtained as a yellow oil.

IR: neat, 2500 broad (2-OH), cm$^{-1}$.

EXAMPLE 52

Preparation of threo-3,4-isopropylidenedioxy-1-octyne

In the manner of Example 45, treatment of a solution of threo-3,4-dihydroxy-1-octyne (Example 51) in dimethoxypropane with 60% perchloric acid, the fractional distillation (12 mm) is productive of the subject compound as a colorless oil, containing 15% of d,l-erthro-3,4-isopropylidenedioxy-1-octyne (Example 60), as an impurity.

IR: neat; 810 (threo configuration).

nmr: CDCl$_3$

TMS; 4.2 (dd, 1, —C≡C—CH—, J's—2H$_z$, 6H$_z$), 4.1–3.9 (m, 1, —C C—CH—C$\underline{H}$—CH$_2$—), 2.5 (d, 1, H—C C—, J=2H$_z$), 1.9–1.2 (m, 14, alkyl), 0.90 (m, 3H, CH$_2$—C$\underline{H}_3$).

EXAMPLE 53

Preparation of erythro-3-tetrahydropyranyloxy-4-hydroxy-1-octyne

Alkaline hydrolysis of d,l-erythro-3-tetrahydropyranyloxy-4-hydroxy-1-trimethylsilyl-1-octyne (Example 43) by the procedure of Example 46 is productive of the subject compound.

EXAMPLE 54

Preparation of erythro-3-tetrahydropyranyloxy-4-methoxy-1-octyne

To a stirred slurry of 6.0 g (150 mmol.) of a 60% oil dispersion of sodium hydride and 96 g of iodomethane, under an argon atmosphere, is added 700 ml of dry tetrahydrofuran. The stirred mixture is cooled to −20° C. and a solution of 30 g (133 mmol.) of erythro-3-tetrahydropyranyloxy-4-hydroxy-1-octyne (Example 53), is added dropwise, followed by 0.1 ml of methanol. The mixture is stirred at ambient temperature for 24 hours, 10 ml of methanol is added, and evaporated. The residue is taken up in ether, washed 3 times with water, dried over magnesium sulfate, and evaporated. The crude product is purified by fractional distillation to yield 16.3 g of a colorless oil, bp 137°–14° C. (12 mm).

EXAMPLES 55–59

By the method of Example 43 reactions of 1-trimethylsilyl-3-tetrahydropyranyloxy-1-propyne with n-butyllithium and subsequent treatment with the aldehydes listed in Table III, below, provides the d,l-erythro-1-trimethylsilyl-3-tetrahydropyranyloxy-4-hydroxy-1-alkynes of the table.

TABLE III

| Ex. | Starting Aldehyde | Product erythro-3-tetrahydropyranyloxy-4-hydroxy-1-trimethylsilyl-1-alkyne |
|---|---|---|
| 55 | n-buanal | erythro-1-trimethylsilyl-3-tetrahydropyranyloxy-4-hydroxy-1-heptyne |
| 56 | n-hexanal | erythro-1-trimethylsilyl-3-tetrahydropyranyloxy-4-hydroxy-1-nonyne |
| 57 | n-heptanal | erythro-1-trimethylsilyl-3-tetrahydropyranyloxy-4-hydroxy-1-decyne |
| 58 | 4-methyl-n-pentanal | erythro-1-trimethylsilyl-3-tetrahydropyranyloxy-4-hydroxy-7-methyl-1-octyne |
| 59 | 2-trans-n-pentenal | erythro-1-trimethylsilyl-3-tetrahydropyranyloxy-4-hydroxy-5-trans-octen-1-yne |

EXAMPLES 60–66

Hydrolysis of the 3-tetrahydropyranyloxy group of the d,l-erythro-1-trimethylsilyl-3-tetrahydropyranyloxy-4-hydroxy-1-alkynes listed in Table IV below by the method describe in Example 44, followed by conversion of the resulting erythro-1-trimethylsilyl-3,4-dihydroxy-1-alkyne to the corresponding d,l-erythro-1-trimethylsilyl-3,4-isopropylidenedioxy-1-alkyne by treatment with dimethoxypropane in the presence of perchloric acid by the method described in Example 45 followed by desilylation to the corresponding erythro-3,4-isopropylidenedioxy-1-alkyne by the procedure of Example 46 followed by treatment with tri-n-butylstannane according to this procedure of Example 2 is productive of the vinylstannyl derivatives of Table IV.

TABLE IV

| Ex. | Starting d,l-erythro-1-trimethylsilyl-silyl-3-tetrahydropyranyloxy-4-hydroxy-1-alkyne of Example | Product erythro-1-iodo-3,4-isopropylidenedioxy-trans-1-alkene |
|---|---|---|
| 60 | 53 | erythro-1-tri-n-butylstannyl-3,4-isopropylidenedioxy-trans-1-heptene |
| 61 | 54 | erythro-1-tri-n-butylstannyl-3,4-isopropylidenedioxy-trans-1-nonene |
| 62 | 55 | erythro-1-tri-n-butylstannyl-3,4-isopropylidenedioxy-trans-1-decene |
| 63 | 56 | erythro-1-tri-n-butylstannyl-3,4-isopropylidenedioxy-7-methyl-trans-1-octene |
| 64 | 57 | erythro-1-tri-n-butylstannyl-3,4-isopropylidenedioxy-trans,trans-1,5-octadiene |
| 65 | 46 | erythro-1-tri-n-butylstannyl-3,4-isopropylidenedioxy-1-octene |
| 66 | 52 | threo-1-tri-n-butylstannyl-3,4-isopropylidenedioxy-1-octene |

EXAMPLES 67-71

Acetylation of the 4-hydroxy group of the erythro-1-trimethylsilyl-3-tetrahydropyranyloxy-4-hydroxy-1-alkynes listed in Table V below by the method described in Example 47, followed by hydrolysis of the resulting erythro-1-trimethylsilyl-3-tetrahydropyranyloxy-4-acetyloxy-1-alkynes to the corresponding erythro-1-trimethylsislyl-3-hydroxy-4-acetyloxy-1-alkynes by the method of Example 49, followed by epimerization to threo-1-trimethylsilyl-3-hydroxy-4-acetyloxy-1-alkynes by the method of Example 50 followed by hydrolysis by the method of Example 51 to give threo-3,4-dihydroxy-1-alkynes are converted to the corresponding threo-3,4-isopropylidenedioxy-1-alkynes by treatment with dimethoxypropane in the presence of perchloric acid by the method described in Example 52 followed by treatment with tri-n-butylstannane by the procedure of Example 2 is productive of the threo vinylstannyl derivatives.

TABLE V

| Ex. | Starting erythro-1-trimethylsilyl-3-tetrahydropyranyloxy-4-hydroxy-1-alkyne of Example | Product threo-1-tri-n-butylstannyl-3,4-isopropylidenedioxy-trans-1-alkene |
|---|---|---|
| 67 | 53 | threo-1-tri-n-butylstannyl-3,4-isopropylidenedioxy-trans-1-heptene |
| 68 | 54 | threo-1-tri-n-butylstannyl-3,4-isopropylidenedioxy-trans-1-nonene |
| 69 | 55 | threo-1-tri-n-butylstannyl-3,4-isopropylidenedioxy-trans-1-decene |
| 70 | 56 | threo-1-tri-n-butylstannyl-3,4-isopropylidenedioxy-7-methyl-trans-1-octene |
| 71 | 57 | threo-1-tri-n-butylstannyl-3,4-isopropylidenedioxy-1,5-trans; trans-1-octadiene |

TABLE V-continued

| Ex. | Starting erythro-1-trimethylsilyl-3-tetrahydropyranyloxy-4-hydroxy-1-alkyne of Example | Product threo-1-tri-n-butylstannyl-3,4-isopropylidenedioxy-trans-1-alkene |
|---|---|---|

EXAMPLES 72-74

Treatment of the alkynes of Table VI with tri-n-butylstannane by the procedure of Example 2 is productive of the vinylstannyl derivatives of the Table.

TABLE VI

| Example | Starting Alkyne | Product Vinylstannyl Derivative |
|---|---|---|
| 72 | 46 | erythro-1-tri-n-butylstannyl-3,4-isopropylidenedioxy-1-octene |
| 73 | 52 | threo-1-tri-n-butylstannyl-3,4-isopropylidenedioxy-1-octene |
| 74 | 54 | erythro-1-tri-n-butylstannyl-3-tetrahydropyranyloxy-4-methoxy-1-octene |

EXAMPLE 75

Preparation of (E)-1-tri-n-butylstannyl-3-methyl-3-trimethylsilyloxy-1-octene

To a solution of 3 g of trans-1,2-bis(tri-n-butylstannyl) ethylene in 15 ml of dry tetrahydrofuran at −78° C. is added 2.5 ml of 2.1 M n-butyllithium. After allowing the solution to warm to −40° C., the solution is transferred to another flask containing 550 mg of 2 heptanone in 10 ml of tetrahydrofuran. After warming to room temperature, the reaction mixture is poured into saturated aq. ammonium chloride and extracted with hexanes. Concentration of the hexanes provides (E)-1-tri-n-butylstannyl-3-methyl-1-octene-3-ol.

The vinylstannane is treated with imidazole, and chlorotrimethylsilane in dimethylformamide by the procedure of Example 1 to provide (E)-1-tri-n-butylstannyl-3-methyl-3-trimethylsilyloxy-1-octene as an oil.

EXAMPLES 76-88

Treatment of the ketones and aldehydes of Table VII by the procedure of Example 75 with trans-1-lithio-2-tri-n-butylstannyl ethylene followed by treatment of the resulting vinylstannylalcohol with the indicated trialkylchlorosilane by the procedure of Example 2 is productive of the vinylstannylsilyloxy products of the Table.

TABLE VII

| Ex. | Starting Ketones and Aldehydes | | Product (Stannyl Derivative) |
|---|---|---|---|
| 76 | 2-octanone | TMS-Cl | (E)-1-tri-n-butylstannyl-3-methyl-3-trimethylsilyloxy-1-nonene |
| 77 | 2-nonanone | TMS-Cl | (E)-1-tri-n-butylstannyl-3-methyl-3-trimethyl-1-decene |
| 78 | 2,2-dimethyl-1-hexanol U.S. Pat. 3,873,607 | TMS-Cl | (E)-1-tri-n-butylstannyl-4,4-dimethyl-3-trimethylsilyloxy-1-octene |
| 79 | 3,3-dimethyl-1-hexanol U.S. Pat. 3,873,607 | TMS-Cl | (E)-1-tri-n-butylstannyl-5,5-dimethyl-3-trimethylsilyloxy-1-octene |
| 80 | 4-ethyl-1-oct-yne-3-ol U.S. Pat. 3,873,607 | TMS-Cl | (E)-1-tri-n-butylstannyl-4-ethyl-3-trimethylsilyloxy-1-octene |

TABLE VII-continued

| Ex. | Starting Ketones and Aldehydes | | Product (Stannyl Derivative) |
|---|---|---|---|
| 81 | 4-methyl-1-heptyne-3-ol U.S. Pat. 3,873,607 | TMS-Cl | (E)-1-tri-n-butylstannyl-4-methyl-3-trimethylsilyloxy-1-heptene |
| 82 | 2,2-trimethylenehexaldehyde Bel. Pat. 843,679 | TMS-Cl | (E)-1-tri-n-butylstannyl-4,4-trimethylene-3-trimethylsilyloxy-1-octene |
| 83 | 2,2-trimethyleneoctaldehyde Bel. Pat. 843,679 | TMS-Cl | (E)-1-tri-n-butylstannyl-4,4-trimethylene-3-trimethylsilyloxy-1-decene |
| 84 | 2,2-trimethylene-3-phenylpropionylaldehyde Bel. Pat 843,679 | TMS-Cl | (E)-1-tri-n-butylstannyl-4,4-trimethylene-3-trimethylsilyloxy-5-phenyl-1-pentene |
| 85 | 2,2-trimethylenehex-4-yn-1-ol Bel. Pat 843,679 | TMS-Cl | (E)-1-tri-n-butylstannyl-4,4-trimethylene-3-trimethylsilyloxy-6-yn-1-octene |
| 86 | 2,2-trimethylenehex-4-cis-en-1-ol Bel. Pat 843,679 | TMS-Cl | (E)-1-tri-n-butylstannyl-4,4-trimethylene-3-trimethylsilyloxy-6-cis-1-octadiene |
| 87 | cyclohexanone | TMS-Cl | 1-[(E)-2-tri-n-butylstannylethylene]-1-trimethylsilyloxycyclohexane |
| 88 | cyclopentanone | TMS-Cl | 1-[(E)-2-tri-n-butylstannylethylene)]-1-trimethylsilyloxycyclopentane |

EXAMPLE 89

Conversion of (E)-1-tri-n-butylstannyl-4-triethylsilyloxy-1-octene to (E)-1-iodo-4-triethylsilyloxy-1-octene and (E)-1-iodo-4-hydroxy-1-octene To a solution of E-1-tri-n-butystannyl-4-triethylsilyloxy-1-octene (11 g) in 200 ml ether is added 0.9 equivalents of iodine in one portion. After 25 minutes the color of the iodine has disappeared. An additional 0.1 equivalents of iodine is added in portions until the iodine color persists. The ether is removed in vacuo to provide (E)-1-iodo-4-triethylsilyloxy-1-octene. This residue is placed on a silica-gel column (240 g SilicAR CC-7) packed in hexane. A liter fraction of hexane contains 7.5 g of mostly tri-n-butyliodostannane. A 500 ml elution of benzene gives only a small amount of material. An elution with 600 ml of ether provides 7.0 g of 1-iodo-4-hydroxy-1-octene as an oil.

EXAMPLE 90

Preparation of (E)-1-tri-n-butylstannyl-3-(2-tetrahydropyranyloxy)-1-octene

A mixture of bis(tri-n-butylstannyl) oxide (42.5 g 71.3 mmol.) and polymethylhydrogen siloxane (9.5 g) is stirred at ambient temperature for 30 minutes. To this mixture is added 3-(2-tetrahydropyranyloxy)-1-octyne (21 g, 100 mmol.) and azobisisobutyronitrile (100 gm). The reaction mixture is warmed to 80° C. whereupon an exothermic reaction occurs. After several additional hours at 80° C., the reaction mixture is distilled under vacuum to provide 16.7 g of the product as an oil (bp 174°-178° C., 0.8 mm).

EXAMPLE 91

Preparation of Ethyl-15-hydroxy-9-oxo-13-trans-prostenoiate

To a solution of (E)-tri-n-butylstannyl-3(2-tetrahydropyranyloxy)-1-octene (10.5 g, 21 mmols) in tetrahydrofuran (8 ml) at −78° C. is added 2.4 M n-butyllithium (8.75 ml; 21 mmols). After 1 hour at −78° C., a solution of copper pentyne mmol) in hexamethylphosphoramide (63 mmol) is added and the solution is stirred at −50° C. for 10 minutes.

The cuprate solution is recooled to −78° C. and 2-(6-carbethoxyheptyl)-2-cyclopentenone (U.S. Pat. No. 3,873,607) (4.77 g, 20 mmols) in tetrahydrofuran (9 ml) is added. The resulting mixture is stirred at −78° C. for 30 minutes and at −10° C. for 90 minutes.

The mixture is poured into saturated aq. ammonium chloride and stirred 18 hours. The organic phase is separated and the blue aqueous phase is extracted several times with ether. The combined ether extracts are washed with 1% sulfuric acid (100 ml), brine and dried over sodium sulfate. The solvents are removed in vacuo to provide an oil. This oil is dissolved in a 4:2:1 solution of HOAC/THF/Water (340 ml) at 55° C. and stirred for 4 hours and then concentrated.

Purification of the residue by silica-gel chromatography to provide 2.7 g of product.

EXAMPLE 92

Preparation of 11,16-dihydroxy-9-oxo-13-trans-prostenoate

To a solution of (E)-1-tri-n-butylstannyl-4-methyl-4-trimethylsilyloxy-1-octene (Example 32) (6.03 g) in tetrahydrofuran (5 ml) at −70° C. is added 2.2 M n-butyllithium (5.5 ml). The solution is warmed to −40° C. for 1 hour and to −30° C. for a further 1 hour.

In a second flask is placed copper pentyne (2.84 g), tri-n-butylphosphine (8.8 g) and ether (25 ml). After 20 minutes at room temperature, the copper pentyne solution is transferred to a −78° C. vinyllithium solution.

After stirring at −78° C. for 2 hours, a solution of 4-trimethylsilyloxy-2-(6-carbotrimethylsilyloxy)cyclopent-2-en-1-one (U.S. Pat. No. 3,873,607) (3.5 g) in ether (8 ml) is added via syringe.

The mixture is stirred at 78° C. for 10 minutes, at −40° C. to −50° C. for 1 hour at −40° C. to −30° C. for 50 minutes. The mixture is recooled to −50° C. and quenched with saturated aq. ammonium chloride (300 ml) and ether (150 ml).

The aqueous solution is extracted with ethyl acetate and the combined organic layers are dried magnesium sulfate and concentrated to an oil.

The oil is dissolved in a mixture of acetic acid (60 ml) tetrahydrofuran (30 ml) and water (15 ml) and stirred under nitrogen at room temperature for 30 minutes. Toluene (100 ml) is added and the mixture is concentrated in vacuo to a viscous oil. Toluene is again added and reconcentrated to constant weight.

The residue is placed onto a column of 18 g of silica-gel and washed with hexane. The hexanes fraction will give about 9 g and contains no prostaglandin product. The silica-gel is flushed with ethyl acetate (200 ml) to provide 5.9 g of prostaglandin materials. This 5.9 g is purified via dry-column chromatography (dcc) on 860 g of silica-gel developing water 4:1 EtOAc/Hexane containing 1% acetic acid. The product containing fraction from the dry-column is removed and extracted with ethyl acetate to provide 1.3 g of pure product and an additional 1.0 g of nearly pure product.

EXAMPLE 93

Conversion of E-1-tri-n-butylstannyl-3-triethylsilyloxy-1-octene (Ex. 2) to E-1-bromo-3-triethylsilyloxy-1-octene and E-1-bromo-3-hydroxy-1-octene.

To a solution of 5.85 g of E-1-tri-n-butylstannyl-3-triethylsilyloxy-1-octene (Example 2) in 6 ml of carbon tetrachloride (CCl$_4$) at −20° C. is added slowly a solution of bromine (1.8 g) in 6 ml of carbon tetrachloride under nitrogen.

After the addition is complete, (a slight yellow color should persist) the solution is allowed to warm to ambient temperature and the solvents are removed in vacuo to provide E-1-bromo-3-triethylsilyloxy-1-octene. This residue is filtered through 60 g of silic-AR CC-7 and washed with 300 ml of hexane. The hexane elutant is concentrated to provide 4.6 g of mostly Bu$_3$Sn-Br.

The silica-gel cake is washed with 300 ml of ether. The ether is concentrated to provide 3.3 g of residue that is mostly E-1-bromo-3-hydroxy-1-octene.

EXAMPLE 94

Treatment of the (E)-1-tri-n-butylstannyl derivatives of Examples 2, 21-40b and 60-88 with iodine.

Treatment with iodine, by the procedure of Example 89, followed by purification, by the procedure of Example 89, will provide the corresponding E-1-iodohydroxy and tri lower alkyl silyloxy (or other protected) derivatives.

EXAMPLE 95

Treatment of the E-1-tri-n-butylstannyl derivatives of Examples 21-40b and 60-88 with bromine.

Treatment with bromine, by the procedure of Example 93, followed by purification by the method of Example 93, is productive of the corresponding E-1-bromo-3-hydroxy and E-1-bromo-4-hydroxy alkenes.

EXAMPLE 96

Preparation of E-1-tri-n-butylstannyl-3-trimethylsilyloxy-4,4-dimethyl-1-octene and Z-1-tri-n-butylstannyl-3-trimethylsilyloxy-4,4-dimethyl-1-octene.

A mixture of 2 g (8.83 mmole) of 3-trimethylsilyloxy-4,4-dimethyl-1-octyne [prepared from 3-hydroxy-4,4-dimethyl-1-octyne U.S. Pat. No. 4,007,210 and chlorotrimethylsilane (Method of Example 1)], 10 mg of azobisisobutyronitrile and 2.09 ml (7.9 mM) of tri-n-butylstannane is stirred in an oil bath under argon atmosphere at ambient temperature and then the temperature is gradually raised to 130° C. The resulting solution is stirred at 130°-135° C. for 2 hours, then cooled to furnish Z-1-tri-n-butylstannyl-3-trimethylsilyloxy-4,4-dimethyl-1-octene. Vapor phase chromatography on a 6′ 5% SE 30 column at an oven temperature of 230° C. shows a peak at retention time of 5.2 minutes. Further treatment of this solution containing the Z isomer with additional tri-n-butylstannane (3-4 mmole) and azobisisobutyronitrile (20 mg) at 130°-135° C. for 4-hour furnishes E-1-tri-n-butylstannyl-3-trimethylsilyloxy-4,4-dimethyl-1-octene. Vapor phase chromatography shows a peak at retention time of 4.7 minutes.

We claim:
1. A compound of the formula:

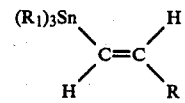

wherein $R_1$ is selected from the group consisting of $C_1$-$C_5$ alkyl; R is selected from the group consisting of

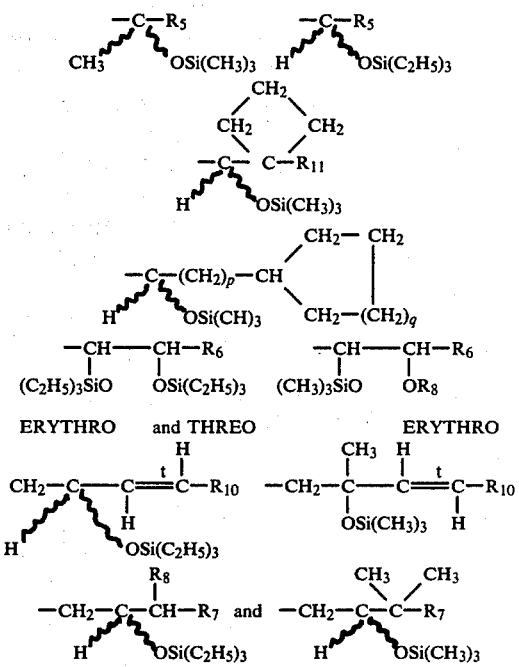

wherein $R_5$ is selected from the group consisting of $C_4$-$C_7$ alkyl, $R_6$ is selected from the group consisting of $C_5$-$C_6$ alkyl $R_7$ is selected from the group consisting of $C_2$-$C_5$ alkyl, $R_8$ is methyl or ethyl, $R_{10}$ is selected from the group consisting of $C_1$-$C_4$ alkyl, $R_{11}$ is selected from the group consisting of $C_3$-$C_6$ alkyl, benzyl, 2-butyne and 2-butene, n is the integer 1 or 2, p is the integer 1 or 2, and q is the integer 1 or 2.

2. A compound according to claim 1, wherein R is as previously defined; and $R_1$ is butyl (CH$_3$CH$_2$CH$_2$CH$_2$—).

3. The compound according to claim 2, (E)-1-tri-n-butylstannyl-3-triethylsilyloxy-1-octene.

4. A compound of the formula

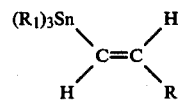

wherein $R_1$ is selected from the group cinsisting of $C_1$ to $C_5$ alkyl; R is selected from the group consisting of

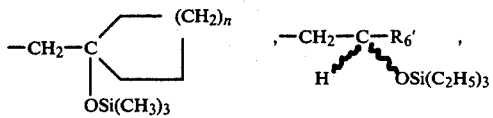

-continued

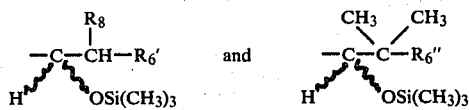

wherein $R_6'$ is selected from the group consisting of $C_3$ to $C_6$ alkyl, $R_6''$ is selected from the group consisting of $C_4$ to $C_6$ alkyl and $R_8$ is methyl or ethyl.

5. The compound of claim 4 wherein R is as previously defined and $R_1$ is butyl ($CH_3CH_2CH_2CH_2$).

6. The compound according to claim 5, (E)-4-triethylsilyloxy-1-tri-n-butylstannyl-1-octene.

7. The compound according to claim 2, (E)-4-triethylsilyloxy-1-tri-n-butylstannyl-1,5-trans-nonadiene.

8. The compound according to claim 2, (E)-4-triethylsilyloxy-5-methyl-1-tri-n-butylstannyl-1-octene.

9. The compound according to claim 2, (E)-4-trimethylsilyloxy-4-methyl-1-tri-n-butylstannyl-1,5-trans-octadiene.

10. The compound according to claim 5, (E)-4(R)-triethylsilyloxy-1-tri-n-butylstannyl-1-octene.

11. The compound according to claim 5, (E)-4(S)-triethylsilyloxy-1-tri-n-butylstannyl-1-octene.

12. The compound according to claim 5, 1-(E-3-tri-n-butylstannyl-2-propenyl)-1-trimethylsilyloxy-cyclohexane.

13. The compound according to claim 5, 1-(E-3-tri-n-butylstannyl-2-propenyl)-1-trimethylsilyloxy-cyclopentane.

14. The compound according to claim 2, (E)-1-tri-n-butylstannyl-3-methyl-3-trimethylsilyloxy-1-octene.

15. The compound according to claim 5, (E)-1-tri-n-butylstannyl-4,4-dimethyl-3-trimethylsilyloxy-1-octene.

16. The compound according to claim 2, (E)-1-tri-n-butylstannyl-4,4-trimethylene-3-trimethylsilyloxy-1-octene.

17. The compound according to claim 2, (E)-1-tri-n-butylstannyl-4,4-trimethylene-3-trimethylsilyloxy-5-phenyl-1-pentene.

18. A compound according to claim 2, (E)-1-tri-n-butylstannyl-4,4-trimethylene-3-trimethylsilyloxy-6-yn-1-octene.

19. The compound according to claim 2, (E)-1-tri-n-butylstannyl-4,4-trimethylene-3-trimethylsilyloxy-6-cis-1-octadiene.

20. The compound according to claim 2, 1-[(E)-2-tri-n-butylstannylethylene]-1-trimethylsilyloxy-cyclohexane.

21. The compound according to claim 2, 1-[(E)-2-tri-n-butylstannylethylene]-1-trimethylsilyloxy-cyclopentane.

* * * * *